United States Patent
Zhu et al.

(10) Patent No.: US 11,352,445 B2
(45) Date of Patent: Jun. 7, 2022

(54) METHOD FOR PREPARING RECOMBINANT PROTEIN FROM BACTERIUM AND COMPOSITION CONTAINING THE SAME

(71) Applicant: JECHO LABORATORIES INC., Frederick, MD (US)

(72) Inventors: Jianwei Zhu, Frederick, MD (US); Cedric Cagliero, Frederick, MD (US); Andrew Burnette, Frederick, MD (US); Yueqing Xie, Frederick, MD (US); Hua Jiang, Frederick, MD (US); Huili Lu, Frederick, MD (US); Manyu Luo, Frederick, MD (US)

(73) Assignee: JECHO LABORATORIES INC., Frederick, MD (US)

( * ) Notice: Subject to any disclaimer, the term of this patent is extended or adjusted under 35 U.S.C. 154(b) by 584 days.

(21) Appl. No.: 16/237,265

(22) Filed: Dec. 31, 2018

(65) Prior Publication Data
US 2020/0207875 A1    Jul. 2, 2020

(51) Int. Cl.
| | | |
|---|---|---|
| *C07K 16/46* | (2006.01) | |
| *C12N 5/00* | (2006.01) | |
| *C12N 15/70* | (2006.01) | |

(52) U.S. Cl.
CPC .......... *C07K 16/461* (2013.01); *C12N 5/0018* (2013.01); *C12N 15/70* (2013.01); *C07K 2317/24* (2013.01); *C07K 2317/55* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell |
| 5,665,866 A | 9/1997 | Weir et al. |
| 5,710,027 A | 1/1998 | Hauptmann et al. |
| 6,602,688 B1 | 8/2003 | Opper et al. |
| 2008/0124765 A1 | 5/2008 | Carter |
| 2011/0244517 A1* | 10/2011 | Simmons ............... C07K 16/00 435/69.6 |

OTHER PUBLICATIONS

Corisedo & Wang, "Functional expression and display of an antibody Fab fragment in *Escherichia coli*: study of vector designs and culture conditions", Protein Expression and Purification, 2004, vol. 34, pp. 270-279. doi:10.1016/j.pep.2003.11.020.*
Ma H, O'Kennedy R., The Structure of Natural and Recombinant Antibodies, Methods Mol Biol. 2015;1348:7-11.
Rosenstain JM, et. al. VEGF in the Nervous System. Organogenesis 2010; 6(2):107-114.
The CATT Research Group., Ranibizumab and Bevacizumab for Neovascular Age-Related Macular Degeneration, New England Journal of Medicine 2011; 364 (20): 1897-1908.

* cited by examiner

*Primary Examiner* — Suzanne M Noakes
(74) *Attorney, Agent, or Firm* — Anova Law Group, PLLC

(57) ABSTRACT

Methods for preparing a recombinant protein from a bacterium are provided. The method includes constructing an expression vector including two promoters. Each of the two promoters attaches a secretion signal peptide to one polypeptide of a protein. The protein attached with the two promoters and secretion signal peptides is then cloned into the expression vector to provide a recombinant expression plasmid. The recombinant expression plasmid is transformed into a host cell. A fermentation process is performed to grow the host cell and to induce an expression to synthesize polypeptides in the host cell and to transport the polypeptides to an outside of a cytoplasm of the host cell, such that the polypeptides are released in a soluble form in a growth medium of the host cell. The polypeptides are assembled into a three-dimensional structure of the protein. The protein is captured from the growth medium.

17 Claims, 4 Drawing Sheets

Specification includes a Sequence Listing.

METHOD FOR PREPARING RECOMBINANT PROTEIN FROM BACTERIUM AND COMPOSITION CONTAINING THE SAME

FIELD OF THE DISCLOSURE

The present disclosure relates to the field of recombinant DNA technology and, more particularly, relates to a method for preparing recombinant proteins from a bacterium and a composition containing the recombinant proteins.

SEQUENCE LISTING

The present application contains a Sequence Listing which has been submitted via EFSWeb and is hereby incorporated by reference in its entirety. The ASCII copy is named "00263sequencelisting.txt" and is 7 kilobytes in size.

BACKGROUND

Antibodies, as one type of protein, have been widely used in research, clinical diagnosis and treatment of diseases. Recombinant DNA technology has made it possible to supply large quantities of antibodies.

The production of antibodies or antibody fragments in bacterial systems has been pursued for many years, particularly in *E. coli* expression systems. Compared to other antibody production systems, *E. coli* provides many unique advantages. For example, the raw materials used (e.g. bacterial cells) are inexpensive and easy to grow, thereby reducing the cost of production. Additionally, fast growth, short generation time and ease of scaling up make bacterial fermentation an attractive means for a large scale of protein production. Further, the genomic structure and biological activity of bacterial species including *E. coli* have been well-studied and a wide range of suitable vectors are available, making expression of a desirable antibody more convenient.

Various approaches have been used to produce recombinant antibodies in bacteria. Naturally occurring antibodies (immunoglobulins) include two heavy chains linked together by disulfide bonds and two light chains, each light chain being linked to one of the heavy chains by disulfide bonds. Like other heterologous proteins, antibody molecules can be obtained from bacteria through refolding of inclusion bodies in the cytoplasm.

Problems arise, however, conventional approaches often result insoluble heavy chains and light chains in the cytoplasm, which require costly and time-consuming purification of the heavy chain and light chain polypeptides. Moreover, the purified polypeptides often cannot form the natural three-dimensional structure of antibodies or antibody fragments, therefore, the conventional approaches may result in the production of antibodies or antibody fragments with low bioactivities.

BRIEF SUMMARY OF THE DISCLOSURE

One aspect of present disclosure provides a method for preparing a recombinant protein from a bacterium. The method includes constructing an expression vector including two promoters. Each of the two promoters attaches a secretion signal peptide to one polypeptide of a protein. The protein attached with the two promoters and secretion signal peptides is then cloned into the expression vector to provide a recombinant expression plasmid. The recombinant expression plasmid is transformed into a host cell. A fermentation process is performed to grow the host cell and to induce an expression to synthesize polypeptides in the host cell and to transport the polypeptides to an outside of a cytoplasm of the host cell, such that the polypeptides are released in a soluble form in a growth medium of the host cell. The polypeptides are assembled into a three-dimensional structure of the protein. The protein is captured from the growth medium.

Another aspect of present disclosure provides a composition, containing the protein captured from the growth medium. The composition further includes a pharmaceutically acceptable carrier. Optionally, the protein includes an antibody fragment. Optionally, the antibody fragment includes an IgG class and Ranibizumab.

Another aspect of present disclosure provides a host cell including the disclosed recombinant expression plasmid.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Figure 1:
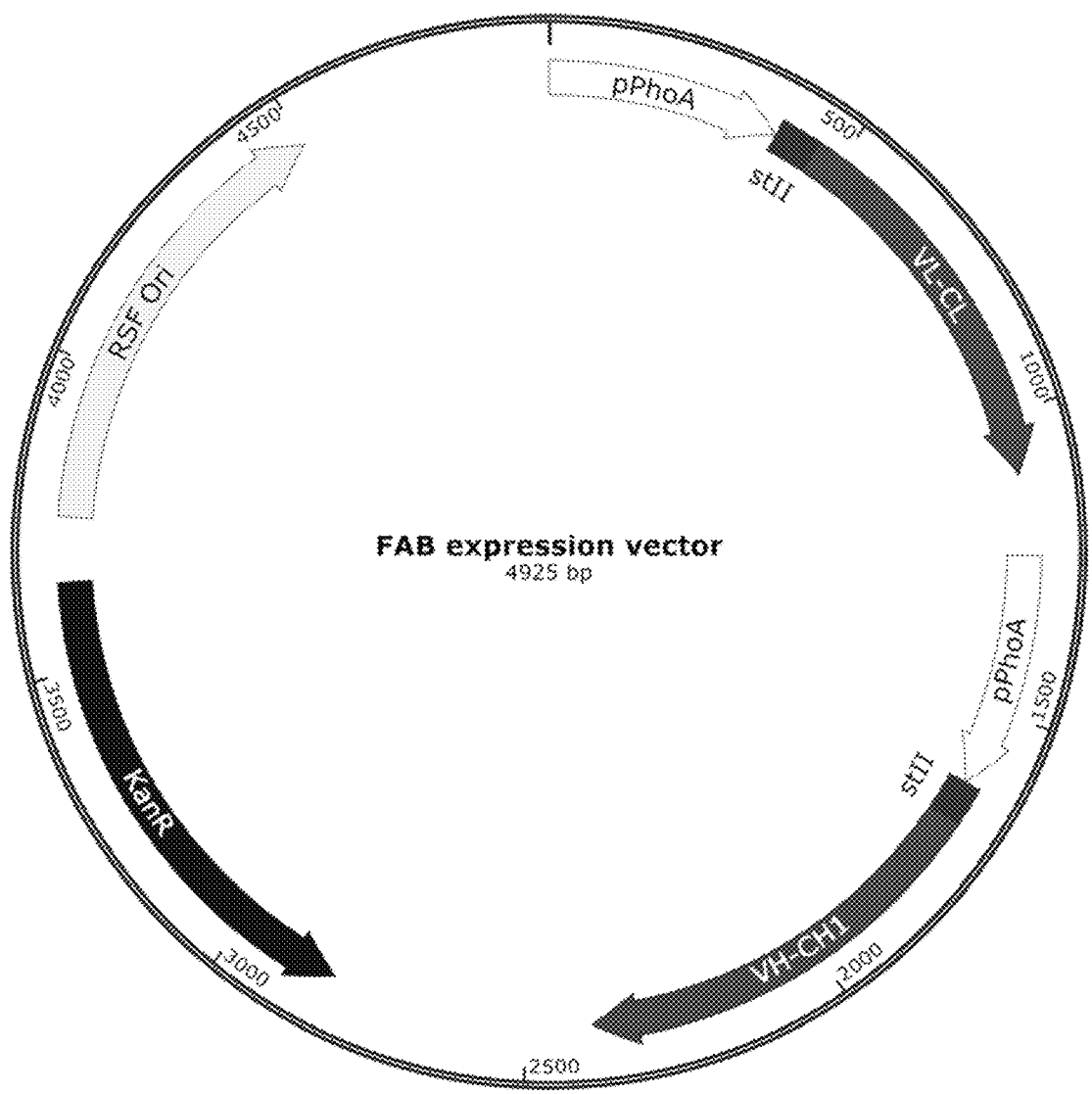
FIG. 1 illustrates an expression plasmid for a production of Ranibizumab consistent with some embodiments of the present disclosure.

Reference will now be made in detail to exemplary embodiments of the disclosure, which are illustrated in the accompanying drawings. Hereinafter, embodiments consistent with the disclosure will be described with reference to drawings. Wherever possible, the same reference numbers will be used throughout the drawings to refer to the same or like parts. It is apparent that the described embodiments are some but not all of the embodiments of the present disclosure. Based on the disclosed embodiments, persons of ordinary skill in the art may derive other embodiments consistent with the present disclosure, all of which are within the scope of the present disclosure.

As used herein, the terms "gene", "recombinant gene", and "gene construct" refer to a nucleic acid of the present disclosure associated with an open reading frame, including both exon and (optionally) intron sequences. A "recombinant gene" refers to nucleic acid encoding a polypeptide and including exon sequences, though it may optionally include intron sequences which are derived from, for example, a related or unrelated chromosomal gene. The term "introit" refers to a nucleic acid sequence present in a given gene which is not translated into protein and may be found between exons. The term "secretion" refers to transportation through the cytoplasmic membrane.

The terms "vector" and "plasmid" are interchangeable, for example, "vector" refers to a parental vector which contains no desired expression genes, and "plasmid" refers to an expression vector constructed by inserting desired expression genes into the parental vector. The term "vector" means a construct, which is capable of delivering, and expressing, one or more genes or sequences of interest in a host cell. Examples of vectors include, hut are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, a "recombinant expression vector" can be any suitable recombinant expression vector which can be used to transform or transfect any suitable host. For example, one of ordinary skill in the art would appreciate that transformation or transfection is a process by which exogenous nucleic acid such as DNA is introduced into a cell, where the transformation or transfection process involves contacting the cell with the exogenous nucleic acid such as the recombinant expression vector as described herein. Non-limiting examples of such expression vectors include the pUC series of vectors (Fermentas Life Sciences), the pBluescript series of vectors (Stratagene, LaJolla, Calif.), the pET series of vectors (Novagen, Madison, Wis.), the pGEX series of vectors (Pharmacia Biotech, Uppsala, Sweden), and the pEX series vectors (Clontech, Palo Alto, Calif.).

As used herein, an "expression cluster" includes at least two genes from the 5' terminus to the 3' terminus of a reading frame, with one being a nucleic acid sequence of an induction promoter-secretion signal peptide gene, the other being a desired nucleic acid sequence of a target protein. A desired nucleic acid sequence of a protein, an antibody or a fragment thereof can be inserted in downstream of the cluster, where the 5' terminus of the exogenous gene is attached to the 3' terminus of the signal peptide gene.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid. For example, the nucleic acid encoding the amino acid presequence of a preprotein or a secretory leader is operably linked to a nucleic acid encoding a polypeptide, where the expressed preprotein participates in the secretion of the polypeptide; a promoter or enhancer is operably linked to a coding sequence if it affects the transcription of the sequence; or a ribosome binding site is operably linked to a coding sequence if it is positioned so as to facilitate translation. "Operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "N-terminus" "5-end" and "5-terminus" are exchangeable, similarly, "C-terminus" "3'-end" and "3-terminus" are exchangeable. In certain embodiments, the end of the DNA or RNA strands that has the fifth carbon in the sugar-ring of the deoxyribose or ribose may be designated at its terminus. A phosphate group attached to the 5'-end permits ligation of two nucleotides, i.e., the covalent binding of a 5'-phosphate group to the 3'-hydroxyl group of another nucleotide, to form a phosphodiester bond. "5-terminus" is commonly known as the beginning of a gene, the counterpart in translated protein is called "N-terminus." The "3'-end" or "3-terminus" of a strand is so named due to it terminating at the hydroxyl group of the third carbon in the sugar-ring, and is known as the tail end, the counterpart of a protein is called "C-terminus."

As used herein, the term "recombinant protein" refers to a protein produced as a result of the transcription and translation of a gene carried by a recombinant expression vector that has been introduced into a host cell. In certain embodiments the recombinant protein is an antibody, for example, a chimeric, humanized, or fully human antibody. In certain embodiments the recombinant protein is an antibody with an isotype selected from a group consisting of: IgG (e.g. IgG1, IgG2, IgG3 and IgG4), IgM, IgA1, IgA2, IgD, and IgE. In certain embodiments, the antibody molecule is a full-length antibody (e.g., an IgG1 or IgG4 immunoglobulin), alternatively the antibody is a fragment (e.g., an Fc fragment or a Fab fragment). In some embodiments, the recombinant protein is a DVD-Ig, a TVD-Ig, a RAB or a half-body.

Amino Acid Sequence Variants. The present disclosure also encompasses amino acid sequence variants of the native antibody or antibody fragment. These variants are prepared by introducing appropriate nucleotides into a suitable plasmid.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

A polypeptide, antibody, polynucleotide, vector, cell, or composition which is "isolated" is a polypeptide, antibody, polynucleotide, vector, cell, or composition which is in a faun not found in nature. Isolated polypeptides, antibodies, polynucleotides, vectors, cells or compositions include those which have been purified to a degree that they are no longer in a form in which they are found in nature. In some embodiments, an isolated form of an antibody, polynucleotide, vector, cell, or composition is substantially pure.

The terms "polypeptide," "peptide," and "protein" are used interchangeably herein referring to polymers of amino acids of any length. The polymer can be linear or branched, it can include modified amino acids, and it can be interrupted by non-amino acids. The terms also encompass an ammo acid polymer that has been modified naturally or by intervention; for example, disulfide bond formation, glycosylation, acetylation, phosphorylation, or any other manipulation or modification, such as conjugation with a labeling component. Also included within the definition are, for example, polypeptides containing one or more analogs of an amino acid (e.g. unnatural amino acids), as well as other modifications known in the art. It is understood that, because the polypeptides of the present disclosure are based upon antibodies, in certain embodiments, the polypeptides can occur as single chains or associated chains.

The term "fusion protein" as used herein refers to a polypeptide which comprises amino-acid sequences from at least two proteins or peptides.

The terms "antibody" and "immunoglobin" as used herein are interchangeable. An antibody is a large, Y-shaped protein produced by the immune system and is used to neutralize antigens. For example, an antibody may recognize a unique molecule from a bacterium or a virus. An antibody may neutralize an antigenic substance produced by tumor cells. Moreover, a patient may produce antibodies which recognize a normal protein or complex proteins from the patient. In an experimental setting, an antibody can be cleaved into Fab fragments and Fc fragments. The Fab fragments contain variable regions (Fv) that bind to specific antigenic substances. To the contrary, the Fc fragments of all antibodies in a class is the same for each species. Antibodies can be categorized into various classes, for example, IgA, IgD, IgE, IgM. In humans, approximately 75% of antibodies in the circulation system belongs to IgG class. IgG or fragments of IgG have been commonly used for therapeutic purposes. For example, Ranibizumab as described herein, an IgG antibody fragment has been found effective in treating age-related macular degeneration.

As mentioned above, the "Fab" fragment is the region of an antibody that binds to antigens. It contains a variable domain and a constant domain of the light chain, as well as a variable domain and a first constant domain (CH1) of the heavy chain. F(ab')$_2$ antibody fragments include a pair of Fab fragments which are covalently linked near their carboxy termini by hinge cysteines between them. In the field of therapeutics, the advantages of using Fab fragments over the whole antibody molecules include: the fragments eliminate non-specific blinding of the Fc regions to cells; efficiently penetrate tissues; and Fab fragments do not interfere with anti-Fc mediated antibody detection. As disclosed herein, exemplary "Fab" fragments may include Ranibizumab, Ganitumab, Trastuzumab, Basiliximab, Denosumab, and Nivolumab.

The term "Fv" is defined herein as an antibody fragment which contains an antigen recognition and binding site. This region includes a dimer containing one variable domain of the light chain and one variable domain of the heavy chain in tight association, which can be covalent in nature, for example, in a single-chain Fv antibody fragment (scFv). Within this configuration, three complementary-determining regions (CDRs) of each variable domain interact to define an antigen binding site on the surface of the $V_H$-$V_L$ dimer. Collectively, the six CDRs or a subset thereof achieve the specific binding of the antibody to the antigen. However, even a single variable domain (or half of an Fv including only three CDRs specific for an antigen) is able to recognize and bind antigen, although with lower affinity as compared to the entire binding site including two variable domains.

"Single-chain Fv" or "scFv" antibody fragments include the $V_H$ and $V_L$ domains of antibody, where these domains are present in a single polypeptide chain. For example, the Fv polypeptide further includes a polypeptide linker between the $V_H$ and $V_L$ domains, which enables the scFv to form the desired structure for antigen binding.

"Cells", "culture cells", or "host cells", "recombinant host cells" refer to subject cells for recombinant DNA manipulations. It would be apparent from the context that, these cells may be candidates for, or resultants of, transfer of the recombinant expression plasmid according to recombinant techniques. The definition further includes the progeny of the cells directly referred to. Such progeny may not be precisely identical in DNA content to their parents, but such progenies are included in the definition so long as alterations because, for example, to accidental or deliberate mutation do not destroy the ability of the cells to exhibit the properties conferred by the DNA introduced.

The phrase "recombinant host cell" (or simply "host cell"), or "positive cell" includes a cell into which a recombinant expression vector has been introduced. It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells selected from any of the Kingdoms of life. In certain embodiments, the host cells used in the methods of the present disclosure are prokaryote, yeast, or eukaryote cells. Suitable prokaryotes for this purpose include eubacteria, such as Gram-negative or Gram-positive organisms, e.g., Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. lichemformis*, *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. It should be noted that these examples are merely for illustrative purposes rather than being limiting.

In certain embodiments, the host cells are eukaryotic microbes such as filamentous fungi or yeast. *Saccharomyces cerevisiae*, or common baker's yeast, is the most commonly used among lower eukaryotic host microorganisms. Besides of the aforementioned host cells, a number of other genera, species, and strains are commonly available and useful herein, such as *Schizosaccharomyces pombe*; *Kluyveromyces* hosts such as, e.g., *K. lactis*, *K fragilis* (ATCC 12,424), K bulgaricus (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

In certain embodiments, the host cells are derived from multicellular organisms. In some embodiments, the cells are invertebrate cells from plant and insect cells. Non-limiting examples include cells derived from *Spodoptera frugiperda* (caterpillar), *Aedesnaegypti* (mosquito), *Aedes albopictus* (mosquito), *Drosophila melanogaster* (fruitfly), *Bombyx mori*, cotton, corn, potato, soybean, petunia, tomato, and tobacco can also be utilized.

The term "culture" used herein refers to a verb, which means cultivating host cells in a growth medium at various temperatures. It also refers to a noun, which include a growth medium with or without host cells.

A "rich medium" refers to a cell culture medium with no limitation on nutritional ingredients. Luria Broth (LB) is most commonly used. Other options include 2× yeast extract-tryptone (YT), Terrific Broth, or Super Broth, or any other suitable growth medium. An example of a rich medium includes about 1% yeast extract, about 2% peptone, and about 1% glucose.

$OD_{600}$ refers to the measurement of the cell concentration by spectrophotometer reading, where an $OD_{600}$ of 1.0 may indicate a cell concentration of approximately $8 \times 10^8$ cells/ml.

"Phosphate limited medium" refers to the concentration of phosphate in the medium is from about 0 to about 20 mM. In the present disclosure, the concentration is controlled so the induction automatically occurs when the cell density (measured by $OD_{600}$) is between about 15 and 20, for example around 8 hours after inoculation. The ingredients of the phosphate-limited medium used in the present disclosure are: about 24 g/L of casamino acids, about 125 of μM $FeCl_3$, about 2.4 mM of isoleucine, about 4.12 mM of sodium citrate, about 59 mM of sulfates, about 20 μM of trace elements, about 3 g/L of glucose and about 8 mM of phosphate. In some of the embodiments, "phosphate limited medium" and "phosphate free medium" are interchangeable, for example, when the phosphate is completely exhausted, or phosphate reagents are not added in the medium.

As used herein, the term "substantially pure" refers to a material substantially free of contaminants. For example, a material may be substantially pure, including at least about 50% pure (i.e., free of contaminants), at least about 90% pure, at least about 95% pure, at least about 98% pure, or at least about 99% pure.

The term "pharmaceutical formulation" refers to a preparation which is in a form of permitting the biological activity of the active ingredient to be effective, meanwhile, containing no additional components unacceptably toxic to a subject to which the formulation would be administered. Such formulation may be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drugs effective to "treat" a disease or disorder in a subject or mammal. In the case of cancer, the therapeutically effective amount of a drug may reduce the number of cancer cells; reduce the tumor size; inhibit (i.e., slow to some extent and in a certain embodiment, stop) the infiltration of cancer cells into peripheral organs; inhibit (i.e., slow to some extent and in a certain embodiment, stop) tumor metastasis; inhibit, to some extent, tumor growth; and/or relieve to some extent one or more symptoms associated with the cancer. To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. A prophylactically effective amount may be less than the therapeutically effective amount, since a prophylactic dose is used in subjects prior to or at an earlier stage of disease. The term "label" refers to a detectable compound or composition conjugated directly or indirectly with the antibody, thereby generating a "labeled" antibody. The label can be detectable by itself (e.g., radioisotope labels or fluorescent labels) or, in the case of an enzymatic label, can catalyze chemical alteration of a substrate compound or composition which is detectable.

As used in the present disclosure and claims, the singular forms "a," "an," and "the" include plural forms unless the context clearly dictates otherwise. It is understood that wherever embodiments are described herein with the language "including," otherwise analogous embodiments described in terms of "consisting of" and/or "consisting essentially of" are also provided.

Various embodiments in the present disclosure provide methods for preparing recombinant proteins, such as an antibody or an antibody fragment, from a bacterium and compositions containing the recombinant proteins. The polypeptides of the protein are secreted into a growth medium of a host cell in a soluble form. The polypeptides then fold and assemble into a natural three-dimensional structure of the protein.

For example, the recombinant proteins may include a variety of antibody fragments including, Rarbizumab, IgG class, and other suitable antibody fragments. In one embodiment, the disclosed methods may be used to produce, for example, Ganitumab (Human IgG1 kappa), Trasmzumab (humanized IgG1 kappa), Denosumb (human IgG2 kappa) and Nivolumab (human IgG4 kappa)

The method according to the embodiments of the present disclosure may include the steps in the following: a) preparing a recombinant DNA expression plasmid; b) transforming the plasmid into host cells, selecting a positive cell in to which the plasmid is transformed; c) performing a fermentation process to grow the host cells, inducing expression of a protein in the host cells, and transporting each polypeptide of the protein outside of cytoplasm of the host cells into a growth medium, such that each polypeptide is released in a soluble form into the growth medium, and form the protein with a natural structure; d) separating the host cells from the growth medium to obtain cell-free fermentation broth (CFFB); and e) capturing the protein from the CFFB; and/or f) further purifying the protein.

In one embodiment, when preparing a recombinant protein from a bacterium, the protein constitutes a single chain polypeptide, or two chains of polypeptides. The two chains of the polypeptides are homologous or heterologous.

In one embodiment of the present disclosure, the method for preparing a recombinant protein includes constructing an expression vector, the expression vector including two promoters; each of the two promoters attaching a secretion signal peptide to a polypeptide of the protein; cloning the protein attached with the secretion signal peptide into the expression vector to provide a recombinant expression plasmid; transforming the recombinant expression plasmid into a host cell; performing a fermentation process to grow the host cell, inducing an expression to synthesize the polypeptides in the host cell, and transporting the polypeptides outside of a cytoplasm of the host cell into a growth medium, where the polypeptides fold into a three-dimensional structure.

In one embodiment of present disclosure, each promoter operably linked to one secretion signal peptide and one polypeptide of the protein, and each promotor induces the expression of one polypeptide of the protein, the promoter includes alkaline phosphatase A promoter (pPhoA). The expression vector further includes an antibiotic selection gene.

In one embodiment of the present disclosure, attaching the secretion signal peptide to the polypeptide includes: attaching the secretion signal peptide to the N-terminus of one of the polypeptides. The secretion signal peptide includes outer membrane protein A (OmpA), heat-stable toxin II (stII), alkaline phosphatase (PhoA), and pectate lyase B (PelB).

In one embodiment of the present disclosure, the secretion signal peptide is heat-stable toxin II (stII).

In one embodiment of the present disclosure, the steps of cloning and transforming include: cloning genes corresponding to the protein into a plasmid under pPhoA promoters; and transforming the plasmid containing the sequences of the protein into the host cell including *E. coli* strain for protein production.

In one embodiment of the present disclosure, each promotor induces the expression of a fusion polypeptide, where the fusion polypeptide includes one secretion signal peptide and one polypeptide of the protein. The secretion signal peptide allows transportation of the polypeptide to the outside of the cytoplasm of the host cell, during which the secretion signal peptide is cleaved from the polypeptide, resulting in the release of the polypeptide in a soluble form into the growth medium.

In one embodiment of the present disclosure, an expression vector is used for the cloning, production and secretion of an antibody or a fragment thereof into a growth medium, where the antibody or the fragment thereof forms a natural 3-dimentional structure. The expression vector includes two promoters; each of the two promoters attaching a secretion signal peptide to a heavy chain or a light chain of the antibody or the fragment thereof. The method according to the embodiments of the present disclosure includes cloning the antibody or the fragment thereof attached with the secretion signal peptide into the expression vector to provide a recombinant expression plasmid; transforming the recombinant expression plasmid into a host cell; performing a fermentation process to grow the host cell and inducing an expression to synthesize fusion proteins constituting the secretion signal peptide together with the heavy chain or the light chain. The secretion signal peptide induces the transportation of the fusion protein outside of the cytoplasm of the host cell, and during the transportation process, the heavy chain and the light chain are cleaved from the fusion proteins, consequently, released in a soluble form into the growth medium.

The heavy chain and light chain are secreted into the growth medium in a soluble form. As a result, the two chains fold and assemble into an antibody or antibody fragment with natural three-dimensional structures in the growth medium. The antibody or antibody fragment is then isolated from the growth medium and further purified. The method avoids complicated purification process and construction of three-dimensional structures which are time consuming, expensive and often result in the loss of bioactivities.

In one embodiment of the present disclosure, the method includes constructing an expression vector, where the expression vector includes two promoters, each of the two promoters attaching a secretion signal peptide to the heavy chain or the light chain of an antibody or a fragment thereof; cloning the heavy chain and the light chain attached with the secretion signal peptide into the expression vector to provide a recombinant expression plasmid; transforming the recombinant expression plasmid into a host cell; performing a fermentation process to grow the host cell, inducing an expression to synthesize the heavy chain and the light chain in the host cell, and transporting the heavy chain and the light chain outside of the cytoplasm of the host cell into the growth medium, where the heavy chain and the light chain fold into an antibody or a fragment thereof with a natural three-dimensional structure.

In one embodiment of the present disclosure, each promoter is operably linked to one secretion signal peptide and one of the heavy chain and the light chain of the antibody or the fragment thereof, and each promoter induces the expression of the heavy chain or the light chain. The promoter includes alkaline phosphatase A promoter (pPhoA). The expression vector further includes an antibiotic selection gene.

In one embodiment of the present disclosure, attaching the secretion signal peptide to the heavy chain or the light chain includes: attaching the secretion signal peptide to the N-terminus of the heavy chain or the light chain. The secretion signal peptide includes outer membrane protein A (OmpA), heat-stable toxin II (stII), alkaline phosphatase (PhoA), and pectate lyase B (PelB).

In one embodiment of the present disclosure, the secretion signal peptide is heat-stable toxin II (stII).

In one embodiment of the present disclosure, the steps of cloning and transforming include: cloning genes corresponding to an antibody or a fragment thereof into a plasmid under pPhoA promoters to provide the expression of the antibody or a fragment thereof and transforming the plasmid containing the sequences of the antibody or the fragment into the host cell including *E. coli* strain for production.

In one embodiment of the present disclosure, each promotor induces the expression of a fusion polypeptide, where each fusion polypeptide includes one secretion signal peptide and one of the heavy chain and the light chain of an antibody or a fragment thereof. The secretion signal peptide allows transportation of the fusion protein to out of the cytoplasm of the host cell, during which the secretion signal peptide is cleaved from the fusion protein. Consequently, the heavy chain or the light chain is secreted into the growth medium in a soluble form. Because each expression plasmid has two promotors with one promotor operably linked to the heavy chain of an antibody or a fragment thereof, and the other promotor operably linked to the light chain of an antibody or a fragment thereof, the heavy chain and the light chain are expressed at 1:1 ratio. Accordingly, the released heavy chain and the light chain fold and assemble into a natural three-dimensional structure of an antibody or a fragment thereof In one embodiment, the present disclosure provides a method for producing recombinant Ranibizumab in a growth medium. The method may significantly simplifies the purification steps because it avoids purifying Ranibizumab from host cell paste which may contaminate host cell protein.

In one embodiment, the present disclosure provides a method for producing Ranibizumab with high bioactivity. The heavy chain and the light chain of Ranibizumab are simultaneously expressed substantially at 1:1 ratio, transported and released into a growth medium in a soluble form such that the heavy chain and the light chain fold and assemble into a natural structure in the growth medium. Steps including complicated purification and construction of three-dimensional structures in which bioactivities are commonly lost are avoided.

In one embodiment, the present disclosure provides a minicircle DNA recombinant parental vector having two sets of gene expression control clusters, and each of the two sets of clusters includes one induction promoter and one secretion signal peptide. The cloning gene of interest can be inserted to the downstream of the control cluster. The induction promoter induces the expression of the downstream gene. Therefore, two desired genes are simultaneously expressed by one vector. As a result, the genes are expressed as two chains of polypeptides at about 1:1 ratio. The parental vector can be used to express proteins or antibodies which constitute two chains of polypeptides. The promotors also induce expression of secretion signal peptides that direct the expressed polypeptides through the cytoplasmic space and then the signal peptides are removed, leaving the two polypeptides, which correctly form a substantial 1:1 dimer in the periplasmic space and the culture medium.

In one embodiment, the present disclosure provides a DNA recombinant parental vector having at least two sets of gene expression control clusters, and each of the clusters includes one induction promoter and one secretion signal peptide sequence. One of coding gene sequences of a protein, antibody or a fragment thereof can be inserted to downstream of each of expression clusters, respectively, where 5' terminus of one coding sequences is attached to the 3' terminus of one of the secretion signal peptides, respectively. The parental vector further includes a selection gene for selecting a host cell containing a parent vector or Ranibizumab expression plasmid.

In some embodiments of the present disclosure, the promoters are *E. coli* alkaline phosphatase A promoters (pPhoA). PhoA promoter is a promoter that the expression can be regulated by phosphate concentration. Very high product yields have been obtained by the use of PhoA system, for example gram per liter yields of an active Fab have been achieved using this system.

Suitable secretion signal peptide genes may include, but not limited to, secretion signal peptides of the outer membrane protein A (OmpA), heat-stable toxin II (stII), Alkaline phosphatase (PhoA), pectate lyase B (PelB), or other in silico optimized secretion peptides.

In one embodiment, the present disclosure provides a fermentation process which includes, for example, a) cultivating positive cells in a phosphate-limited medium at about 30° C. to 42° C. until the density of the cells reaches the range of about 1.0 to 40.0 (OD600), or, growing the plasmid-containing host cells in a rich medium at about 30° C. to 42° C. until the density of the cells reaches the range from about 1.0 to 40.0 (OD600), followed by replacing the rich medium with a phosphate-free medium; b) continuing cultivating the cells in the phosphate-free medium at about 18° C. to 30° C. for about 2 to 24 hours, for example, at 20° C., then cultivating the cells at about 45° C. to 65° C. for about 0.5 to 2 hours, during which the polypeptides of the antibody are released in a soluble form into the phosphate-free medium; c) rapidly cooling culture temperature to about 10° C. to 30° C.; and/or d) collecting the medium to capture the target product for further purification.

In one embodiment, the present disclosure provides a method for producing a protein, such as an antibody or a fragment thereof, during which the folding and assembling of the heavy chain and the light chain of the antibody are accelerated by incubating the bacteria culture at an elevated temperature below Fab's melting point, for example, at a temperature from about 25° C. to 65° C., such as from about 45° C. to 65° C., for about 30 min to 2 hours after the induction phase. The solubility of the heavy chain and the light chain may be increased in the growth medium, and a three-dimensional structure may be automatically formed in the growth medium. The culture is then cooled down to room temperature. The cells are removed from the culture medium and discarded. The antibody or a fragment thereof is purified by suitable methods from the cell free fermentation broth (CFFB). An exemplary method is to capture the antibody by suitable tools including a Protein L column or the like, and subsequently purified to homogeneity using ion-exchange chromatographic methods.

In some embodiment, solubility of the polypeptides is increased by incubating the bacteria culture at temperature from about 25° C. to 65° C. The increase in the solubility may contributes in forming the natural three-dimensional structure in the growth medium.

In some embodiments, the present disclosure provides a method for producing antibody fragments including anti IGF-R Fab fragment of Ganitumab, anti Her2 Fab fragment of Trastuzumab, anti CD25 Fab fragment of Basiliximab, anti RANKL Fab fragment of Denosumab, anti PD-1 Fab fragment of Nivolumab. In particular, DNA sequences corresponding to each Fab fragment are cloned into the expression vector, then the vector containing the DNA sequences is transformed into *E. Coli*. BL 21 (B strain) cells. Then, the Fab fragments are expressed by the disclosed fermentation process as described above. One of the exemplary processes may include: the *E. Coli*. cells are grown in a rich medium until the cell density reaches an $OD_{600}$ of about 1.0. Then the cells are spun down resuspended in a phosphate-limited medium, and cultivated in the phosphate limited medium at about 18° C. for about 16 hours. After that, the cells are cultivated at an elevated temperature below the melting point of the expressed antibody fragment, and then cultivated at a decreased temperature of about 4° C. to 30° C. After the cultivation, cell-free medium was harvested by centrifugation and the target antibody fragments are captured by the use of Protein L columns, followed by further purification.

In one embodiment, the present disclosure provides a method for producing Ranibizumab by which the heavy chain and the light chain are synthesized substantially at 1:1 ratio in one host cell and transported through the periplasmic space to the growth medium. Antibody fragment heavy and light coding sequences The nucleic acids encoding the heavy chain and the light chain of the antibody fragment, respectively, are each attached to the C-terminus of one of the secretion signal peptides that direct the recombinant protein to the periplasmic space. The secretion signal peptides are removed during the transportation through the cytoplasmic membrane, leaving the intact heavy chain and light chain, which are released into the culture medium. The heavy chain and the light chain are automatically folded and assembled into a natural structure either in the periplasmic or the culture medium. Ranibizumab is then captured from the growth medium and further purified. Ranibizumab may be produced with high bioactivities in a fast and cost-effective manner because complicated steps to purify and refold the three-dimensional structure of Ranibizumab may be avoided.

An exemplary method for manufacturing Ranibizumab includes: a) attaching the 5' terminus of the nucleic acid sequence encoding the heavy chain of Ranibizumab and the nucleic acid sequence encoding the light chain of Ranibizumab, respectively, to 3' terminus of the nucleic acid sequence encoding one of the stII secretion signal peptides, and inserting the polynucleotides of the secretion signal peptides and the nucleic acid sequences of the heavy chain or the light chain into the downstream of one of the *E. coli* alkaline phosphatase A promoters to form a Ranibizumab expression plasmid; b) transforming the expression plasmid into a host cell; c) cultivating the host cell containing the Ranibizumab expression plasmid in a phosphate-limited medium at about 30° C. to 42° C. until the density of the cells reaches the range of about 1.0 to 40.0 ($OD_{600}$), or, growing the plasmid-containing host cell in a rich medium at about 30° C. to 42° C. until the density of the cells reaches the range from about 1.0 to 40.0 ($OD_{600}$), then, replacing the rich medium with a phosphate-free medium; d) continuing cultivating the cells in the phosphate-free medium at about 18° C. to 30° C. for about 2 to 24 hours, for example at 20°

C., then cultivating the cells at about 45° C. to 65° C. for about 0.5 to 2 hours, during which the polypeptides of the antibody are released into growth medium in a soluble form; e) rapidly cooling culture temperature to about 10° C. to 30° C.; and/or f) collecting the growth medium, capturing Ranibizumab with protein L, and further purifying Ranibizumab.

In one embodiment, the present disclosure provides an expression plasmid for simultaneously producing at least two polypeptides in one host cell. The plasmid includes at least two expression clusters. Each of the two clusters includes: from 5'-end to 3'-end, a promoter-secretion signal peptide, as a desired to be expressed sequence. In some embodiments, the cluster includes: 5'-end to 3'-end, a pPhoA promoter—heat stable toxin II peptide gene, as a desired to be expressed sequence.

In one embodiment, the present disclosure provides an expression plasmid for simultaneously producing both the heavy chain and the light chain of Ranibizumab in a host cell. The sequences of the heavy chain and the light chain are inserted at downstream of one promotor, respectively. The promotor induces the expression of the heavy chain or the light chain of Ranibizumab. The polynucleotide sequence of each chain is attached to the 3'-end of a secretion signal peptide.

In one embodiment, the present disclosure provides a cloning process of Ranibizumab which includes transforming the host cell with a vector. The vector includes a nucleic acid with the sequence shown as SEQ ID NO: 1, encoding the heavy chain of Ranibizumab having an amino acid sequence shown as SEQ ID NO: 2, where 5'-end of the nucleic acid with the sequence of SEQ ID NO: 1 is attached to the 3'-end of a nucleic acid encoding a secretion signal peptide. The vector further includes a nucleic acid with the sequence shown as SEQ ID NO: 3, encoding the light chain of Ranibizumab having an amino acid sequence shown as SEQ ID NO: 4, where 5'-end of the nucleic acid with the sequence of SEQ ID NO: 3 is attached to the 3'-end of a nucleic acid encoding another secretion signal sequence.

In one embodiment, the present disclosure provides a method for treating a disease caused by over-expression of CD47 or over-expression of VEGF, or both, including administering to a patient or a subject with therapeutically effective amount of Ranibizumab.

In an exemplary embodiment, the present disclosure provides a method to produce antibodies. The antibodies can be of any species, a rat, a rabbit, or a goat. In some embodiments, the antibodies are human antibodies. In some embodiments, the antibody is a natural, humanized or chimeric antibody, and other antibodies known in the art.

It is of particular convenience in producing humanized antibodies. Humanized antibodies are chimeric antibodies including non-human and human regions and have reduced immunoreactivity when used in humans for therapeutic purposes. For example, the variable domains of the antibodies are of non-human origin and the constant domains of the antibodies are of human origin. Humanized antibodies can also be produced by inserting non-human complementarity-determining-regions (CDRs) into the framework of a human antibody. Nucleic acid sequences encoding a humanized antibody of interest can be inserted to a vector and the antibody may be produced according to the method described in the exemplary embodiments of the present disclosure. For example, oligonucleotides encoding CDRs with desired antigen-recognition properties are used to replace the CDR regions in a human antibody gene. In certain instances, mouse monoclonal antibody may have the desired antigen recognition characteristics. These CDR-encoding regions are sequenced and oligonucleotides encoding these regions are inserted into the human antibody gene. By inserting integrated oligonucleotide sequences into the vector, the step of constructing the expression plasmid may be accomplished. Accordingly, one with ordinary skill in the art may obtain a humanized antibody by following other steps of the method described in the embodiments of the present disclosure.

The disclosure described herein provides a method for preparing recombinant antibody fragments. Antibody fragments according to the disclosure may be from different nature or classes. In some embodiments, the antibody fragments include Fab fragments or antigen-binding regions such as scFv which belong to immunoglobulin class IgG1, IgG2, IgG3 or IgG4.

The produced antibody or antibody fragment according to the present disclosure may be of significance in various applications, including functioning as a research tool, a diagnostic molecule, or a manufacture to treat diseases. An illustrative antibody is Ranibizumab an anti-vascular endothelial growth factor (VEGF) antibody that inhibits the activity of vascular endothelial growth factor A (VEGF-A). VEGF family has five members in mammals, and among others, VEGF-A is highly expressed in acute and sub-acute stages of central nervous system injury. VEGF plays a pivot role in the growth of abnormal blood vessels. Therefore, VEGF is closely associated with diseases caused by abnormal blood vessel growth, and, VEGF-A inhibitors are potential candidates for treating such diseases. For example, age-related macular degeneration (AMD) is one of the leading causes of blindness among elderly patients in developed countries. Ranibizumab has been approved to treat the "wet" type of AMD. The vascular pathology of AMD shares certain similarities with diabetic retinopathy, although the cause of diseases and the typical source of neovascularization differ between the two diseases. The U.S. Food and Drug Administration expanded the approved use of Ranibizumab to treat diabetic retinopathy (DR) in patients with diabetic macular edema (DME) in 2015. Because of its inhibition in angiogenesis, Ranibizumab has been strategically applied in the treatment of malignant tumors and metastases.

The present disclosure provides a method for producing and secreting two or more polypeptides into a growth medium after expression of the polypeptides in prokaryotes which can be carried out in a simple manner. The polypeptides are released in a soluble form into the growth medium, where the polypeptides are folded and assembled in a natural form without laborious in vitro post-treatment, for example, without disruption of prokaryotic cells, solubilization, reduction and renaturation of inclusion bodies. In an exemplary embodiment, the polypeptides form a protein, an antibody, or an antibody fragment in the growth medium. The antibody or antibody fragment may have any desired antigen specificity. For example, the antibody or antibody fragment may bind specifically to a species and cell-specific antigen, such as a human tumor antigen, a natural killer cell receptor, etc.

In some embodiments, a recombinant expression plasmid is constructed by inserting encoding sequences of desired polypeptides into an empty or parental plasmid. The term of empty vector referred to the vector has no encoding sequences of desired polypeptides, an antibody, or an antibody fragment. The empty vector has two or more promoters and two or more suitable secretion signal peptide genes. The vector also contains other elements that are necessary for DNA replication, antibiotic(s) selection, and gene expression. Suitable secretion signal peptides may include but not limited to the secretion signal of the outer membrane protein A (OmpA), heat-stable toxin II (stII), alkaline phosphatase (PhoA), pectate lyase B (PelB), or other in silico optimized secretion peptides.

Expression and cloning plasmids may contain a promoter that is recognized by the host organism and is operably linked to a encoding nucleic acid sequence of an antibody or a fragment, for example, a Fab fragment. Promoters are untranslated sequences located upstream (5') to the start codon of a Fab structural gene (for example, within about 100 to about 1000 bp) that control its transcription and translation. Such promoters may include, for example, inducible promoters and constitutive promoters. Inducible promoters are promoters that initiate increased levels of transcription from DNA under their control in response to some change in culture conditions, e.g., the presence or absence of a nutrient or a change in temperature.

In some embodiments, the promoters, the nucleic acid encoding the secretion signal peptides, and the nucleic acid encoding the target polypeptides may form expression clusters. In an exemplary embodiment, one expression vector may contain at least two expression clusters, where each cluster may include the nucleic acid encoding one of the target polypeptides, therefore, two polypeptides can be simultaneously expressed at about 1:1 ratio in one host cell, and then the secretion signal peptides drive the two polypeptides to the cytoplasmic space where the two polypeptides are cleaved from the signal peptides and released to the growth medium. The two polypeptides may fold and assemble into a three-dimensional structure in the growth medium.

Inducible promoters under high regulation may be suitable for the microbial expression of Fv-containing polypeptides. A large number of promoters recognized by a variety of potential host cells are well known. These promoters are operably linked to DNA encoding the Fab polypeptide by removing the promoter from the source DNA by restriction enzyme digestion and inserting the isolated promoter sequence into the vector. Both the native Fab polypeptide promoter sequences and many non-native Fab polypeptide promoters may be used to direct amplification and/or expression of the Fab polypeptide DNA. Non-native Fab polypeptide promoters may be preferred, as they may permit higher yields in the transcription expression of target polypeptides as compared to using native target polypeptide promoters.

The present disclosure requires the vector has two or more of the same or heterologous inducible promoters, for example, two of the same inducible promoters, such that each polypeptide is expressed at the same rate. Promoters suitable for use with prokaryotic hosts may include the β-lactamase and lactose promoter systems, alkaline phosphatase, a tryptophan (trp) promoter system and hybrid promoters such as the tac promoter. Besides of the aforementioned promoters, other known bacterial promoters may also be suitable.

In an exemplary embodiment, an expression plasmid may have two E. coli alkaline phosphatase A (PhoA) promoters. A phoA promotor may induce targeted gene expression in a reduced phosphate concentration. Installment of two identical PhoA promoters may enable each polypeptide that is operably linked to each of the two promoters to be expressed at same rate, such as the production of each polypeptide molecules at a substantial 1:1 ratio.

Secretion of polypeptides into the periplasmic space of E. coli and other prokaryotes or into their culture media is subject to a variety of parameters. For example, vectors for secretion of a polypeptide of interest may be engineered to link the DNA encoding a secretory signal sequence to the DNA encoding the polypeptide of interest. In an exemplary embodiment, heat stable toxin II (stII) may be used.

DNA sequence encoding a polypeptide is prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier-prepared variant or a non-variant version of the target polypeptide or by total gene synthesis. These techniques may utilize nucleic acid (DNA or RNA) encoding the target polypeptides, or nucleic acids complementary to the nucleic acids encoding the target polypeptides. Oligonucleotide-mediated mutagenesis is a preferred method for preparing substitution, deletion, and insertion variants of target polypeptide DNA.

Preparation of the expression plasmid can be achieved by standard ligation techniques. Targeted DNA fragments are cleaved, tailored, and re-ligated to generate the desired expression plasmid.

In some exemplary embodiments, the expression plasmid is constructed such that the encoding sequences of a light and a heavy chain are inserted downstream of each E. coli alkaline phosphatase A promoters (pPhoA), respectively, i.e., one phoA promoter induces the expression of either a light chain polypeptide, or a heavy chain polypeptide. The heavy and light encoding sequences are individually attached to the 3' terminus of one of secretion signal peptides, so that, one promotor induces the expression of a fusion protein of a signal peptide and the heavy chain, the other promotor induces the expression of a fusion protein of a signal peptide and the light chain. The signal peptides direct the recombinant proteins to the cytoplasmic space, where the heavy chain and light chain are cleaved from the signal peptides and released into growth medium.

According to the embodiments of the present disclosure, a fermentation process may include: a) cultivating positive cells in a phosphate-limited medium at about 30° C. to about 42° C. until the density of the cells is in the range from about 1.0 to about 40.0 ($OD_{600}$), or, growing the plasmid-containing host cells in a rich medium at about 30° C. to about 42° C. until the density of the cells is in the range from about 1.0 to about 40.0 ($OD_{600}$), then, replacing the rich medium with a phosphate free medium; b) continuing cultivating the cells in a phosphate free medium at about 18° C. to about 30° C. for about 2 to about 24 hours, for example at about 20° C., then cultivating the cells at about 45° C. to about 65° C. for about 0.5 to about 2 hours, at this time, the polypeptides are released into growth medium in a soluble form; c) decreasing the temperature of the cell culture to about 10° C. to about 30° C.; f) collecting cell-free culture medium, i.e. cell free fermentation broth (CFFB); and/or d) capturing the target product from the CFFB and further purifying the polypeptides.

The expression plasmid is transferred into an E. coli host cell by transformation for protein expression. Suitable host cells for expressing polypeptides are microbial cells such as yeast, fungi, and prokaryotes.

In an exemplary embodiment of the disclosure, suitable prokaryotes include eubacteria, such as Gram-negative or Gram-positive organisms, for example, E. coli, Bacilli such as B. subtillis, Pseudomonas species such as P. aeruginosa, Salmonella typhimurium, or Serratia marcescens. One exemplary E. coli cloning host is BL 21 (ATCC PTA-5073), although other strains such as *E. coli* B, *E. coli* X1776 (ATCC 31,537), *E. coli* RV308 (ATCC 31,608) and *E. coli* W3110 (ATCC 27,325) are suitable. These examples are illustrative rather than limiting. In one embodiment, the host cell may secrete minimal amounts of proteolytic enzymes, and additional protease inhibitors may desirably be incorporated in the cell culture.

Host cells are transfected and transformed with the above-described expression or cloning plasmids of the present disclosure and cultured in conditions as appropriate for inducing promoters, selecting transformants, or amplifying the genes encoding the desired sequences.

In some embodiments, recombinant protein expression is induced by phosphate starvation. For example, the cells can be grown in a phosphate-limited medium that will support autoinduction when phosphate is depleted. The phosphate concentration in the medium is adjusted to support cell growth until the desired cell density is reached. Alternatively, medium development can be avoided if the growth medium is replaced before induction by a phosphate free medium. Cell growth can be performed at a temperature varying from about 30° C. to about 42° C. without affecting the production of the final product. Cell density at induction may vary greatly and be in the range from about 1.0 to about 40.0 ($OD_{600}$). Induction temperature may be lower than the growth temperature, ranged from about 18° C. to about 30° C. When the heavy chain and the light chain are synthesized in the bacterial cells, they are transported outside the cytoplasm through the periplasmic space to the growth medium. During the transition through the cytoplasmic space the signal peptides are removed, leaving the intact heavy and light chains, which correctly form a 1:1 hetero-dimer in the periplasmic space and the culture medium. The dimer formation is also accelerated by incubating the bacteria culture after the induction phase at an elevated temperature below Fab's melting point at temperature from about 45° C. to about 65° C. for about 30 min to about 2 hours.

Purification of targeted polypeptides. The present disclosure provides a method to produce a protein, an antibody, or an antibody fragment by prokaryotic host cells. Purification of the final product is greatly simplified because the polypeptides are released at a 1:1 ratio into growth medium, where the polypeptides are correctly folded into a natural structure. The final products can be further purified by suitable methods according the chemical characteristics of the final product. For example, cells are removed from the culture medium and discarded. The Fab in the culture medium is captured by Protein L from the cell free fermentation broth (CFFB), and subsequently purified to homogeneity using ion-exchange chromatographic methods.

Another aspect of the present disclosure is to provide a recombinant Ranibizumab expression plasmid. Each of the expression plasmid includes two sets of expression control clusters, namely, one phoA promotor and one stII secretion signal peptide gene. The 5'terminus of the coding sequence of the light chain and the coding sequence of the heavy chain are attached to the 3' terminus of one the of stII secretion signal peptide genes, respectively. The expression of each chain is induced by one of the phoA promotors.

Another aspect of the disclosure is to provide a cloning process of Ranibizumab which includes transforming the host cell with a vector. The vector includes a nucleic acid with the sequence as shown in SEQ ID NO: 1, and the nucleic acid encodes the heavy chain of Ranibizumab which has an amino acid sequence as shown in SEQ ID NO: 2. The 5'-end of the nucleic acid with the sequence as shown in SEQ ID NO: 1 is attached to the 3'-end of a nucleic acid encoding a secretion signal peptide (stII: SEQ ID NO: 5). SEQ ID NO: 3 is the sequence of the nucleic acid encoding the light chain of Ranibizumab which has an corresponding amino acid sequence as shown in SEQ ID NO: 4, where the 5'-end of the SEQ ID NO: 3 is attached to the 3'-end of the other secretion signal sequence.

```
Heavy chain nucleotide sequence (SEQ ID NO: 1):
5'-3'
GAAGTCCAACTGGTCGAATCGGGTGGTGGTCTGGTCCAACCGGGTGGCTCG

CTGCGTCTGTCCTGTGCTGCGTCGGGCTATGATTTTACCCATTACGGTATG

AACTGGGTCCGTCAGGCACCGGGTAAAGGTCTGGAATGGGTGGGCTGGATT

AATACCTACACGGGTGAACCGACCTATGCGGCCGATTTTAAACGTCGCTTT

ACGTTCTCTCTGGACACCTCGAAAAGCACGGCATATCTGCAGATGAACAGT

CTGCGCGCGGAAGATACCGCCGTGTATTACTGCGCGAAATACCCGTATTAC

TATGGCACGTCCCACTGGTATTTTGACGTTTGGGGCCAAGGTACCCTGGTC

ACCGTGAGCTCTGCGTCGACCAAAGGTCCGAGCGTGTTCCCGCTGGCACCG

AGTTCCAAATCTACCAGTGGCGGTACGGCAGCTCTGGGTTGTCTGGTTAAA

GATTATTTTCCGGAACCGGTTACCGTCTCCTGGAATTCAGGCGCACTGACC

TCTGGTGTGCATACGTTCCCGGCTGTTCTGCAGTCATCGGGCCTGTACAGC

CTGAGCTCTGTGGTTACCGTTCCGAGTTCCTCACTGGGTACCCAAACGTAT

ATCTGCAACGTCAATCACAAACCGAGTAATACGAAAGTGGACAAAAAAGTT

GAACCGAAAAGTTGCGACAAAACCCATCTGTGA

Heavy chain amino acid sequence (SEQ ID NO: 2):
N terminus-C terminus
EVQLVESGGG LVQPGGSLRL SCAASGYDFT HYGMNWVRQA

PGKGLEWVGW INTYTGEPTY AADFKRRFTF SLDTSKSTAY

LQMNSLRAED TAVYYCAKYP YYYGTSHWYF DVWGQGTLVTVSSASTKG

PS VFPLAPSSKS TSGGTAALGC LVKDYFPEPV TVSWNSGALT SGVH

TFPAVLQSSGLYSLSS VVTVPSSSLG TQTYICNVNH KPSNTKVDKK

VEPKSCDKTH L

Light chain nucleotide sequence (SEQ ID NO: 3):
5'-3'
GACATTCAACTGACCCAAAGTCCGTCCTCGCTGTCTGCTTCCGTCGGTGAC

CGTGTTACCATTACCTGTTCGGCATCCCAAGATATTTCTAACTATCTGAAT

TGGTACCAGCAAAAACCGGGTAAAGCACCGAAAGTCCTGATTTATTTTACC

AGCTCTCTGCATTCCGGCGTTCCGTCACGTTTTAGCGGCTCTGGTAGTGGC

ACCGATTTCACCCTGACGATCAGTTCCCTGCAGCCGGAAGACTTTGCTACG

TATTACTGCCAGCAATACAGCACCGTGCCGTGGACGTTCGGTCAGGGCACC

AAAGTTGAAATTAAACGTACGGTTGCGGCCCCGTCTGTCTTTATCTTCCCG

CCGAGTGATGAACAGCTGAAATCGGGTACCGCAAGCGTGGTTTGTCTGCTG

AACAATTTCTATCCGCGCGAAGCAAAAGTCCAGTGGAAAGTGGACAACGCT

CTGCAGTCCGGCAATTCACAAGAATCGGTGACCGAACAAGATAGCAAAGAC

TCTACGTACAGTCTGTCATCGACCCTGACGCTGTCCAAAGCGGATTATGAA

AAACACAAAGTTTACGCCTGCGAAGTTACGCATCAGGGTCTGTCATCCCCG

GTTACCAAATCGTTTAATCGTGGCGAATGTTGA
```

```
Light chain amino acid sequence (SEQ ID NO: 4):
N terminus-C terminus
DIQLTQSPSS LSASVGDRVT ITCSASQDIS NYLNWYQQKP

GKAPKVLIYF TSSLHSGVPSRFSGSGSGTD FTLTISSLQP

EDFATYYCQQ YSTVPWTFGQ GTKVEIKRTV AAPSVFIFPPSDEQLKSG

TA SVVCLLNNFY PREAKVQWKV DNALQSGNSQ ESVTEQDSKD STYS

LSSTLTLSKADYEKHK VYACEVTHQG LSSPVTKSFN RGEC

StII secretion signal nucleotide sequence (SEQ ID
NO: 5): 5'-3'
ATGAAAAAGAATATCGCATTTCTTCTTGCATCTATGTTCGTTTTTTCTATT

GCTACAAACGCGTACGCT
```

Another aspect of the disclosure, it provides Ranibizumab, which has high affinity for Vascular endothelial growth factor A (VEGF-A). VEGF-A is biological component that can trigger angiogenesis, which is the growth of new blood vessels. Various diseases, including inter alia, ischemia, anemia, peripheral vascular disease, and atherosclerotic lesions can be treated by increasing angiogenesis. This is accomplished by stimulating the up-regulation of VEGF-A, thereby leading to increased blood circulation, hence increased oxygen supply, in the diseased tissue. Ranibizumab is a recombinant humanized IgG1 kappa isotype monoclonal antibody that inhibits VEGF activity by competitively binding to the receptor binding site of active forms of VEGF-A, including the biologically active, cleaved form of this molecule, VEGF110. Hence, Ranibizumab prevents binding of VEGF-A to its principle receptors VEGFR1 and VEGFR2 found on the surface of endothelial cells. This results in reduced endothelial cell proliferation, vascular leakage, and new blood vessel formation.

Ranibizumab has been found effective in treating a panel of diseases. For example, in the eye, excessive vascularization can result in blood and fluid leaking into the eye. These leaky blood vessels can contribute to macular edema and choroidal neovascularization, resulting in the wet type of age-related macular degeneration (AMD). The result of AMD can be the loss of visual acuity or even blindness. Therefore, control of excessive macular vascularization is important in the treatment of macular degeneration. As such, it is a goal of medical professionals to provide a treatment for controlling or curing AMD without inhibiting the beneficial effects of normal VEGF-A activity in the rest of the body. Ranibizumab has been found to be an effective treatment of AMD.

Normal human retinal or not contain little VEGF, or do not contain, however, by hypoxia, caused upregulation of VEGF production. The disease state characterized by VEGF upregulation induced hypoxia, including CRVO and BRVO. The hypoxia-induced upregulation of VEGF can be inhibited pharmacologically. Anti-VEGF antibody, to be able to inhibit capillary endothelial cell proliferation VEGF propulsion has been revealed. Thus, by weakening the effect of VEGF, treating macular edema from venous occlusive disease it is theoretically evidenced.

The present disclosure also provides a pharmaceutical composition including anti-VEGF antibody fragments produced by the disclosed method. Such compositions include a therapeutically or prophylactically effective amount of the polypeptide or protein in admixture with pharmaceutically acceptable materials, and physiologically acceptable formulation materials. The optimal pharmaceutical composition may be determined by one skilled in the art depending upon, for example, the intended route of administration, delivery format, and desired dosage. Such compositions may influence the physical state, stability, rate of in vivo release, and rate of in vivo clearance of the polypeptide. For example, suitable compositions may be water for injection, physiological saline solution for parenteral administration.

The primary vehicle or carrier in a pharmaceutical composition may be either aqueous or non-aqueous in nature. Further, the therapeutic composition may be formulated as a lyophilizate using appropriate excipients such as sucrose.

The formulations can be delivered in a variety of methods, for example, by inhalation therapy, orally, or by injection. When parenteral administration is contemplated, the therapeutic compositions for use in the present disclosure may be in the form of a pyrogen-free, parenterally acceptable aqueous solution including the desired polypeptide in a pharmaceutically acceptable vehicle.

In some embodiments, pharmaceutical formulations suitable for injectable administration may be formulated in aqueous solutions and may contain substances that increase the viscosity of the suspension, such as sodium carboxymethyl cellulose, sorbitol, or dextran. Additionally, suspensions of the active compounds may be prepared as appropriate oily injection suspensions. In another embodiment, a pharmaceutical composition may be formulated for inhalation. Inhalation solutions may also be formulated with a propellant for aerosol delivery, in yet another embodiment, solutions may be nebulized. It is also contemplated that certain formulations may be administered orally. In one embodiment of the present disclosure, molecules that are administered in this fashion can be formulated with or without those carriers customarily used in the compounding of solid dosage forms such as tablets and capsules. In another embodiment, Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, starch, sodium carboxymethyl cellulose, or gums. If desired, disintegrating or solubilizing agents may be added. Dragee cores may be used in conjunction with suitable coatings, such as concentrated sugar solutions, and dyestuffs or pigments may be added to the tablets or dragee coatings for product identification or to characterize the quantity of active compound, i.e., dosage.

Pharmaceutical preparations that can be used orally may also include push-fit capsules made of gelatin, as well as soft, sealed capsules made of gelatin and a coating, such as glycerol or sorbitol. Push-fit capsules main contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Additional pharmaceutical compositions will be evident to those skilled in the art, including formulations involving polypeptides in sustained- or controlled-delivery formulations.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present disclosure is directed to kits for producing a single-dose administration unit. The kits may each contain both a first container having a dried protein and a second container having an aqueous formulation. Also included within the scope of the present disclosure are kits containing single and multi-chambered pre-filled syringes (e.g., liquid syringes and lyo syringes).

An effective amount of a pharmaceutical composition to be employed therapeutically will depend, for example, upon the therapeutic context and objectives. One skilled in the art will appreciate that the appropriate dosage levels for the treatment will thus vary depending, in part, upon the molecule delivered, the indication for which the polypeptide is being used, the route of administration, and the size (body weight, body surface or organ size) and condition (the age and general health) of the patient. The route of administration of the pharmaceutical composition is in accordance with known methods. In some cases, the Ranibizumab antibody fragment of the present disclosure, or an antibody fragment made by the present disclosed method can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are, for example, biocompatible, semi-permeable polymeric enclosures or membranes that allow the release of the polypeptide product(s) but prevent the destruction of the cells by the patient's immune system or by other detrimental factors from the surrounding tissues.

Gene therapy in vivo is also envisioned where a nucleic acid molecule encoding the antibody fragment of the present disclosure, or a derivative thereof is introduced directly into a subject. For example, a nucleic acid encoding an antibody fragment of the present disclosure is introduced into target cells via local injection of a nucleic acid construct with or without an appropriate delivery plasmid, such as an adeno-associated virus plasmid. Alternative non-limiting viral plasmids may include retroviruses, adenovirus, herpes simplex vims and papilloma virus plasmids. Physical transfer of the virus plasmid may be achieved in vivo by local injection of the desired nucleic acid construct or other appropriate delivery plasmid containing the desired nucleic acid sequence, liposome- mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present disclosure is to provide a method for treating cancer using the pharmaceutical composition of the present disclosure including administrating an effective amount of the aforementioned pharmaceutical composition to the patients or subjects in need thereof. In one embodiment, the pharmaceutical composition is used to treat CD47-overexpressing tumors or cancers, including but not limited to acute myeloid leukemia (AML), chronic myeloid leukemia (CML), acute lymphoblastic leukemia (ALL), non-Hodgkin's lymphoma (NHL), multiple myeloma (MM), bladder cancer, ovarian cancer, prostate cancer, lung cancer, colon cancer, breast cancer, pancreatic cancer and renal cancer.

In one embodiment, the pharmaceutical composition can be used to treat other related conditions where CD47 is over-expressed, including but not limited to Crohn's disease, allergic asthma, rheumatoid arthritis.

In one embodiment, the pharmaceutical composition can be used in disease treatment in which it is desired to inhibit the function or activity of VEGF, including but not limited to age-related macular degeneration (AMD), diabetic retinopathy (DR), liver fibrosis, angiosarcoma, etc.

Table 1 lists key specifications for producing two polypeptides by one expression plasmid.

TABLE 1

| Parameters | Values |
|---|---|
| Type of antibody fragments | Fv, Fab, BITE, DART |
| IgG class | IgG1, IgG2, IgG4 |
| Secretion signal peptides | Any (example: StII, OmpA, PhoA, PelB, . . . ) |
| Expression promoters | pPhoA or phosphate inducible promoters |
| Vector selection | Any (example: Kanamycin, ampicillin, . . . ) |
| Plasmid replication origin | Any (example: pACYC, pBR322, pRSF1030) |
| Host cell line | E. coli (example: BL21, T7 express, . . . ) |
| Induction of expression | Phosphate starvation |
| Heat treatment temperature | About 45° C. to 65° C. |
| Heat treatment length | At least 10 min |

EXAMPLES

Production and Secretion of Ranibizumab Into Growth Medium

A Fab fragment corresponding to the antigen VEGF (Ranibizumab) was be produced according to the present disclosure. A stll secretion signal peptide was attached to the N-terminus of the heavy chain or light chain of Ranibizumab. The DNA sequence of each gene was optimized for expression in E. coli and cloned into the plasmid with the use of a pPhoA promoter (FIG. 1). For example, one stll secretion peptide sequence was placed at the 5' terminus region of light chain sequence or heavy chain sequence. Sequences of both the heavy and light chains were present in the same plasmid and both were under control of inducible pPhoA promoters.

Figure 2:
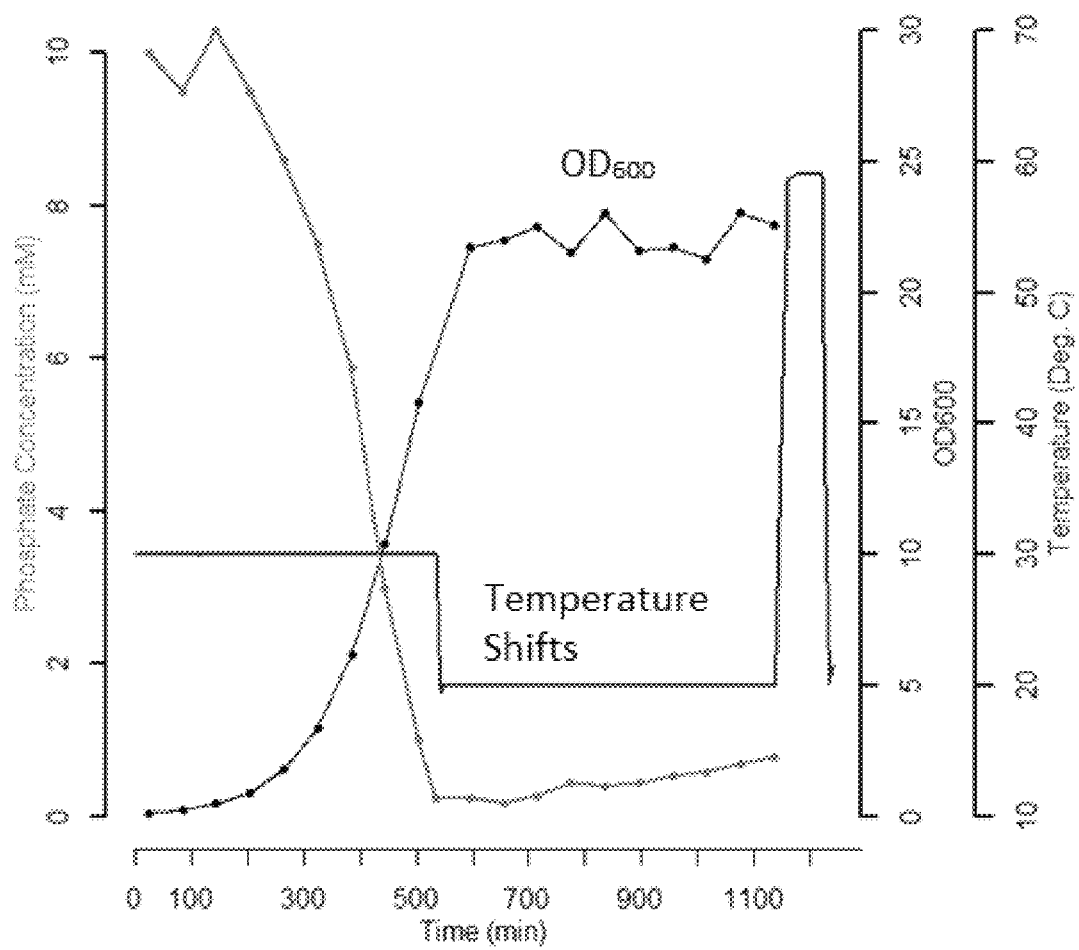
FIG. 2 illustrates a growth profile in a bioreactor of an *E. coli* BL21 strain containing an expression plasmid consistent with some embodiments of the present disclosure.

The plasmid containing both the heavy chains and the light chains was transformed into E. coli BL21(AI) strain for protein production. Seed was prepared overnight for fermenter inoculation. The fermentation process included two main stages, namely, a growth stage at 30° C. followed by an induction stage at 20° C. The production process was carried out through a fed-batch fermentation process with a base medium including approximately 24 g/L of casamino acid, 125 µM of $FeCl_3$, 2.4 mM of isoleucine, 4.12 mM of sodium citrate, 59 mM of sulfates, 20 µM of trace elements, 3 g/L of glucose and 8 mM of phosphate. Fermenter was seeded at 2% and the growth phase was carried out at about 30° C. with a constant dissolved oxygen (DO) level of about 30% and a glucose level maintained between about 0.5 g/L and 1 g/L. The concentration of phosphate in the fermentation medium was optimized such that the induction automatically occurred when the cell density (measured by $OD_{600}$) was between about 15 and about 20, for example around 8 hours after inoculation. Oxygen supplementation may be necessary for maintaining the DO level during the growth phase. When the phosphate concentration was dropped below about 0.4 mM, the temperature of the tank was reduced to about 20° C. and the DO level was increased to about 60%. The entire induction phase took about 10 hours. After the induction, the temperature of the tank was increased to about 59° C. for about 1 hour, and then decreased to about 25° C. During the heat treatment process, the DO level was maintained at about 60% (FIG. 2).

After heat treatment, the cells and the medium were separated by centrifugation at 10,000×g for about 15 min at about 2-8° C. The medium fraction (cell-free fermentation broth—CFFB) containing the secreted Ranibizumab Fab fragments was stored at about 2-8° C. for less than about 24 hours before clarification by depth filtration (Sartorius PB2 filter) and microfiltration (Sartopore 2 filter).

Figure 3:
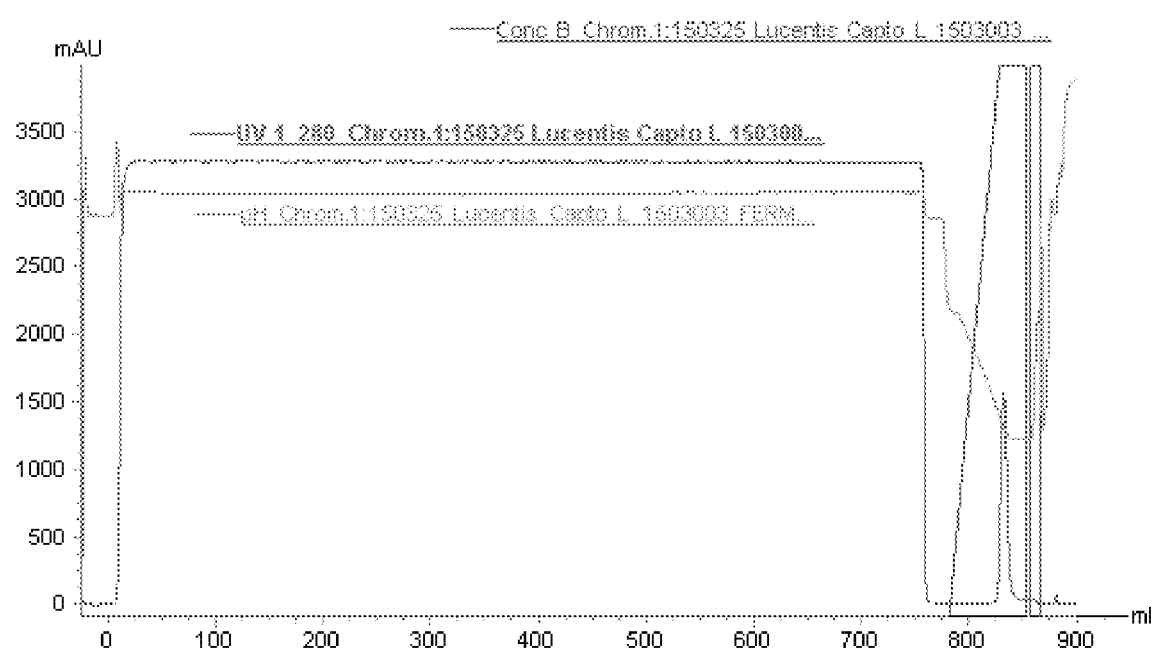
FIG. 3 illustrates a chromatogram showing absorbance of a cell growth medium at 280 nm, where the growth medium contains 50 mM citrate and has a pH value of 3.0 consistent with some embodiments of the present disclosure.
Figure 4:
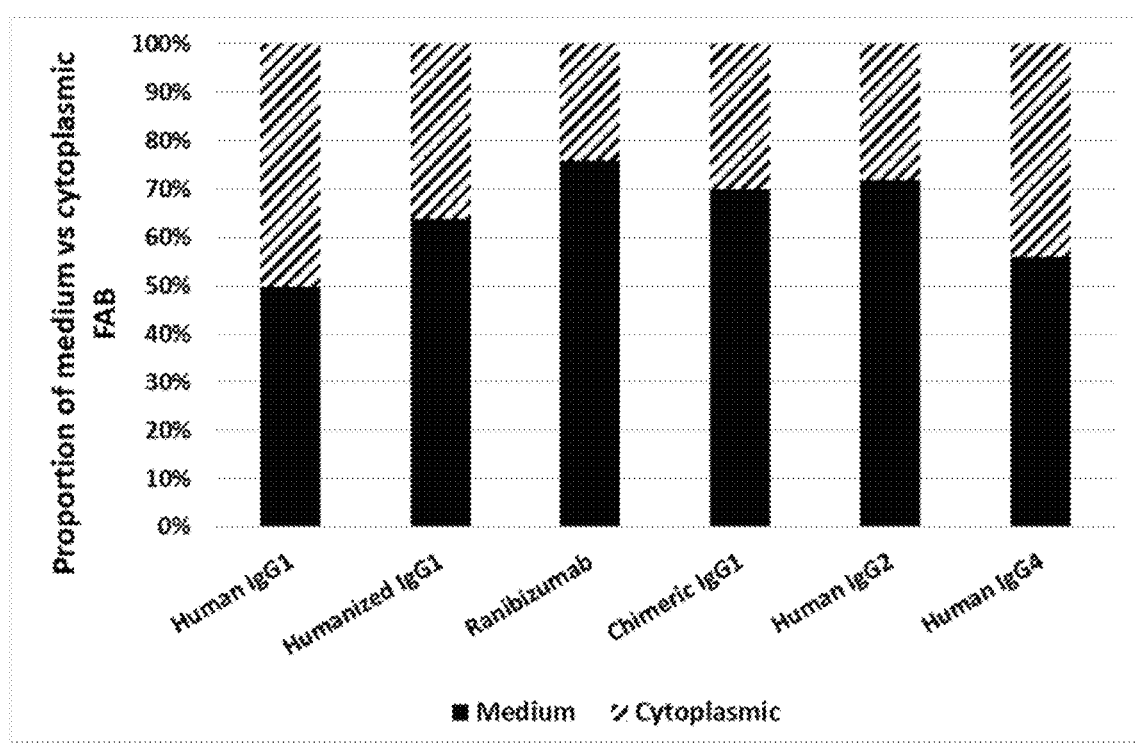
FIG. 4 illustrates medium secretion of IgGs including human IgG1, humanized IgG1, Ranibizumab, chimeric IgG1, human IgG2, and human IgG4 consistent with some embodiments of the present disclosure.

The filtrate was then concentrated approximately by 10 fold and diafiltered by hollow fiber tangential flow filtration (TFF) method, using 10 KDa MWCO hollow fiber membrane (GE Healthcare, Chicago, Ill.). The concentrated fermentation broth was loaded onto a Protein L column (GE HiScreen Capto L column) to separate Ranibizumab from impurities (FIG. 3). The low pH eluate from the Protein L column was subsequently processed through a Capto SP (GE HiScreen Capto SP ImpRes column) in capture mode and a Capto Q Fast Flow (GE HiScreen Capto Q column) in flow-through mode. The purified Ranibizumab was concentrated and formulated in a buffer containing 10 mM histidine HCl, 10% α,α-trehalose dihydrate, 0.01% polysorbate 20, pH 5.5, and stored at -20° C.

Production and Secretion of Antibody Fragments of the IgG Class.

In some embodiments, the IgG class may include, for example, human IgG1, humanized IgG1, chimeric IgG1, human IgG2, and human IgG4. Ganitumab (Anti IGF-R), Trastuzumab (Anti Her2), Basiliximab (Anti CD25), Denosumab (Anti RANKL), and Nivolumab (Anti PD-1) are Fab fragments belonging to the class of human IgG1, humanized IgG1, chimeric IgG1, human IgG2, and human IgG4, respectively. The fragments were produced by the disclosed method. For example, the nucleic acids encoding each FAB fragment were cloned into Fab expression vector and transformed into E. coli BL21 (B strain). Protein expression was performed in the following: cells carrying the plasmid expressing Fab fragments were grown in LB (10 g/L tryptone, 5 g/L yeast extract and 10 g/L NaCl) at 37° C., until the cell density reaches an $OD_{600}$ of 1.0. After that, cells were spun down, and the pellet was resuspended in 1 volume of phosphate limited medium (containing 1 g/L $(NH_4)_2SO_4$, 49 mg/L $MgSO_4$, 2 g/L glucose, 33.6 g/L PIPES, with pH of 7.0) and placed at about 18° C. for about 16 hours for protein induction followed by 60-minute incubation at 59° C. Cell-free medium was then harvested by centrifugation and loaded into protein L column as described above. Cell paste was lysed by chemical method and loaded into protein L column as described above. More than approximately 50% of the product can be recovered from the cell-free growth medium.

Although the present disclosure is disclosed above with various embodiments, the present disclosure is not limited thereto. Anyone skilled in the art may make various changes and modifications without departing from the spirit and scope of the present disclosure. Therefore, the scope of the present disclosure should be defined by the claims thereof.

What is claimed is:

1. A method for preparing a recombinant protein from a bacterium, comprising:
   constructing an expression vector including two promoters, each of the two promoters attaching a secretion signal peptide to one polypeptide of a protein;
   cloning the protein attached with the two promoters and secretion signal peptides into the expression vector to provide a recombinant expression plasmid;
   transforming the recombinant expression plasmid into a host cell;
   performing a fermentation process to grow the host cell and to induce an expression to synthesize polypeptides in the host cell and to transport the polypeptides to an outside of a cytoplasm of the host cell, such that the polypeptides are released in a soluble form in a growth medium of the host cell, wherein the polypeptides are assembled into a three-dimensional structure of the protein, wherein performing the fermentation process includes:
      growing the host cell until a density of grown cells is in a range from 1.0 to 40.0 ($OD_{600}$);
      increasing a temperature to 45° C. to 65° C., followed by a rapid cooling to 4° C. to 30° C. to promote secretion of a heavy chain and a light chain; and
   capturing the protein from the growth medium.

2. The method according to claim 1, wherein capturing the protein includes:
   separating the host cell from the growth medium to provide a cell free fermentation broth; and
   harvesting the cell free fermentation broth for protein purification to obtain the protein.

3. The method according to claim 1, wherein:
   each promoter is operably linked to one secretion signal peptide and the one polypeptide of the protein, and
   each promotor induces an expression of the operably linked polypeptide.

4. The method according to claim 1, wherein:
   the expression vector further includes an antibiotic selection gene.

5. The method according to claim 4, wherein the cloning and the transforming include:
   cloning genes corresponding to the protein into a plasmid under the pPhoA promoters to provide an expression of the protein; and
   transforming the plasmid containing sequences of the polypeptide or two polypeptides of the protein into the host cell including *E. coli* strain for protein production.

6. The method according to claim 1, wherein the secretion signal peptide is attached to an N-terminus of the one polypeptide of the protein, wherein:
   the secretion signal peptide includes one or more of outer membrane protein A (OmpA), heat-stable toxin II (stII), Alkaline phosphatase (PhoA), and pectate lyase B (PelB).

7. The method according to claim 6, wherein the secretion signal peptide is the heat-stable toxin II (stII).

8. The method according to claim 1, wherein:
   each promotor induces an expression of a fusion polypeptide, the fusion polypeptide including one secretion signal peptide and the one polypeptide of the protein, and
   the secretion signal peptide transports the one polypeptide to the outside of the cytoplasm of the host cell, and the two polypeptides are cleaved from the secretion signal peptide and released into the growth medium.

9. The method according to claim 8, wherein the two polypeptides are homologous and constituted by one polypeptide, or the two polypeptides are heterologous constituted by at least two different polypeptides.

10. The method according to claim 1, wherein the protein includes an antibody fragment, one of the two promoters is operably linked to a heavy chain of an antibody fragment, and another of the two promoters is operably linked to a light chain of the antibody fragment.

11. The method according to claim 10, wherein:
    each promotor induces an expression of a fusion polypeptide, the fusion polypeptide including one secretion signal peptide and one of the heavy chain and the light chain of the antibody fragment, and
    the secretion signal peptide transports one of the heavy chain and the light chain to the outside of the cytoplasm of the host cell, and
    the heavy chain and the light chain are cleaved from the secretion signal peptide and released into the growth medium.

12. The method according to claim 11, wherein:
    the heavy chain and light chain are in a soluble form and fold into a heterodimer of the antibody fragment in the growth medium.

13. The method according to claim 10, wherein performing the fermentation process includes:
    growing the host cell in a bio-reactor using a phosphate limited medium at a temperature ranging from 30° C. to 42° C. until a density of the grown cells is in a range from 1.0 to 40.0 ($OD_{600}$);
    continuing cultivating the host cells at 18° C. to 30° C. for 2 to 24 hours; and
    increasing a temperature in the bio-reactor to 45° C. to 65° C., followed by a rapid cooling to 4° C. to 30° C. to promote secretion of a heavy chain and a light chain.

14. The method according to claim 10, wherein performing the fermentation process includes:
    growing the host cell using a rich medium at a temperature ranging from 30° C. to 42° C. until a density of the grown cells is in a range from 1.0 to 40.0 ($OD_{600}$);
    replacing the rich medium with a phosphate free medium, and continuing cultivating the host cells at 18° C. to 30° C. for 2 to 24 hours; and
    increasing the temperature to 45° C. to 65° C., followed by a rapid cooling to 4° C. to 30° C. to promote secretion of a heavy chain and a light chain.

15. The method according to claim 10, wherein:
    the antibody fragment includes an IgG class, wherein:
    the IgG class includes one or more of IgG1, IgG2, and IgG4, and
    the IgG class includes a human, chimeric, or humanized IgG.

16. The method according to claim 1, wherein the protein includes an antibody fragment.

17. The method according to claim 16, wherein the antibody fragment includes an IgG class and Ranibizumab.

* * * * *

SEQUENCE LISTING

```
<160> NUMBER OF SEQ ID NOS: 5

<210> SEQ ID NO 1
<211> LENGTH: 696
<212> TYPE: DNA
<213> ORGANISM: Artifical Sequence
<220> FEATURE:
<223> OTHER INFORMATION: Nucleotide Sequence of Heavy Chain of
      Ranibizumab; Ranibizumab is a humanized murine IgG antibody
      fragment.

<400> SEQUENCE: 1
gaagtccaac tggtcgaatc gggtggtggt ctggtccaac cgggtggctc gctgcgtctg      60
tcctgtgctg cgtcgggcta tgattttacc cattacggta tgaactgggt ccgtcaggca     120
ccgggtaaag gtctggaatg ggtgggctgg attaatacct acacgggtga accgacctat     180
gcggccgatt ttaaacgtcg ctttacgttc tctctggaca cctcgaaaag cacggcatat     240
ctgcagatga acagtctgcg cgcggaagat accgccgtgt attactgcgc gaaatacccg     300
tattactatg gcacgtccca ctggtatttt gacgtttggg gccaaggtac cctggtcacc     360
gtgagctctg cgtcgaccaa aggtccgagc gtgttcccgc tggcaccgag ttccaaatct     420
accagtggcg gtacggcagc tctgggttgt ctggttaaag attattttcc ggaaccggtt     480
accgtctcct ggaattcagg cgcactgacc tctggtgtgc atacgttccc ggctgttctg     540
cagtcatcgg gcctgtacag cctgagctct gtggttaccg ttccgagttc ctcactgggt     600
acccaaacgt atatctgcaa cgtcaatcac aaaccgagta atacgaaagt ggacaaaaaa     660
gttgaaccga aaagttgcga caaaacccat ctgtga                              696

<210> SEQ ID NO 2
<211> LENGTH: 231
```

```
<212> TYPE: PRT
<213> ORGANISM: Artifical Sequence
<220> FEATURE:
<223> OTHER INFORMATION: Heavy Chain of Ranibizumab; Ranibizumab is a
      humanized murine IgG antibody fragment.

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Leu
225                 230

<210> SEQ ID NO 3
<211> LENGTH: 645
<212> TYPE: DNA
<213> ORGANISM: Artifical Sequence
<220> FEATURE:
<223> OTHER INFORMATION: Nucleotide Sequence of light Chain of
      Ranibizumab; Ranibizumab is a humanized murine IgG antibody
      fragment.

<400> SEQUENCE: 3
gacattcaac tgacccaaag tccgtcctcg ctgtctgctt ccgtcggtga ccgtgttacc      60
attacctgtt cggcatccca agatatttct aactatctga attggtacca gcaaaaaccg     120
ggtaaagcac cgaaagtcct gatttatttt accagctctc tgcattccgg cgttccgtca     180
cgttttagcg gctctggtag tggcaccgat ttcacgctga cgatcagttc cctgcagccg     240
gaagactttg ctacgtatta ctgccagcaa tacagcaccg tgccgtggac gttcggtcag     300
ggcaccaaag ttgaaattaa acgtacggtt gcggcccgt ctgtctttat cttcccgccg     360
agtgatgaac agctgaaatc gggtaccgca agcgtggttt gtctgctgaa caatttctat     420
```

```
ccgcgcgaag caaaagtcca gtggaaagtg acaacgctc tgcagtccgg caattcacaa      480
gaatcggtga ccgaacaaga tagcaaagac tctacgtaca gtctgtcatc gaccctgacg      540
ctgtccaaag cggattatga aaaacacaaa gtttacgcct gcgaagttac gcatcagggt      600
ctgtcatccc cggttaccaa atcgtttaat cgtggcgaat gttga                     645
```

<210> SEQ ID NO 4
<211> LENGTH: 214
<212> TYPE: PRT
<213> ORGANISM: Artifical Sequence
<220> FEATURE:
<223> OTHER INFORMATION: Light Chain of Ranibizumab; Ranibizumab is a
      humanized murine IgG antibody fragment.

<400> SEQUENCE: 4

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 69
<212> TYPE: DNA
<213> ORGANISM: Artifical Sequence
<220> FEATURE:
<223> OTHER INFORMATION: Synthetic Nucleotide Sequence

<400> SEQUENCE: 5

```
atgaaaaaga atatcgcatt tcttcttgca tctatgttcg ttttttctat tgctacaaac      60
gcgtacgct                                                             69
```